US009161790B2

(12) United States Patent
Kuxhaus et al.

(10) Patent No.: US 9,161,790 B2
(45) Date of Patent: Oct. 20, 2015

(54) ADJUSTABLE LENGTH ORTHOPEDIC DEVICE

(71) Applicant: Clarkson University, Potsdam, NY (US)

(72) Inventors: Laurel Kuxhaus, Potsdam, NY (US); Alexander Martin Clark, Potsdam, NY (US)

(73) Assignee: Clarkson University, Potsdam, NY (US)

( * ) Notice: Subject to any disclaimer, the term of this patent is extended or adjusted under 35 U.S.C. 154(b) by 12 days.

(21) Appl. No.: 13/908,628

(22) Filed: Jun. 3, 2013

(65) Prior Publication Data

US 2013/0325008 A1    Dec. 5, 2013

Related U.S. Application Data

(60) Provisional application No. 61/654,248, filed on Jun. 1, 2012.

(51) Int. Cl.
A61B 17/72 (2006.01)
A61B 17/74 (2006.01)
A61B 17/86 (2006.01)

(52) U.S. Cl.
CPC ........... *A61B 17/7216* (2013.01); *A61B 17/725* (2013.01); *A61B 17/7233* (2013.01); *A61B 17/744* (2013.01); *A61B 17/8685* (2013.01)

(58) Field of Classification Search
CPC ........ A61B 17/56; A61B 17/66; A61B 17/72; A61B 17/7216; A61B 17/744; A61B 17/8685
USPC ......... 606/55, 57, 58, 59, 246, 258, 259, 260, 606/264, 63, 68, 320, 326, 90, 105
See application file for complete search history.

(56) References Cited

U.S. PATENT DOCUMENTS

| 2,346,346 | A | * | 4/1944 | Anderson ........................ 606/56 |
| 2,687,720 | A | * | 8/1954 | Haboush ........................ 606/54 |
| 3,900,025 | A | * | 8/1975 | Barnes, Jr. ........................ 606/71 |
| 5,766,179 | A | * | 6/1998 | Faccioli et al. ................. 606/98 |
| 2008/0177334 | A1 | | 7/2008 | Stinnette |
| 2011/0230883 | A1 | * | 9/2011 | Zahrly et al. .................... 606/63 |

OTHER PUBLICATIONS

International Search Report Form PCT/ISA237, International Application No. PCT/US2013/043900, pp. 1-10, dated Dec. 11, 2014.

* cited by examiner

Primary Examiner — Pedro Philogene
Assistant Examiner — David C Comstock
(74) Attorney, Agent, or Firm — Blaine T. Bettinger; George R. McGuire; Bond Schoeneck & King, PLLC

(57) ABSTRACT

An adjustable length orthopedic device and system. According to one embodiment, the adjustable length orthopedic device or system comprises an elongated shaft with a longitudinal axis, and an adjustable portion extending from a proximal end of the elongated shaft along the longitudinal axis. The adjustable length orthopedic device further comprises at least one hole in a distal end portion of the device, where the hole is adapted for insertion of a pin through the device and into the bone in order to anchor the device to the bone. According to another embodiment is a lag screw extending from a proximal end of the elongated shaft at an angle oblique to the longitudinal axis, the lag screw comprising a lag screw shaft segment, and an adjustable segment that extends from the proximal end of the shaft segment. According to another embodiment is an adjustable length locking screw.

14 Claims, 6 Drawing Sheets

ADJUSTABLE LENGTH ORTHOPEDIC DEVICE

CROSS-REFERENCE TO RELATED APPLICATIONS

This application claims priority to U.S. Provisional Patent Application Ser. No. 61/654,248, filed on Jun. 1, 2012 and entitled "Adjustable Length Orthopedic Device (ALOD)," the entire disclosure of which is incorporated herein by reference.

BACKGROUND OF THE INVENTION

1. Field of the Invention

The present specification relates to an orthopedic device, and, more specifically, to an adjustable length orthopedic device.

2. Description of the Related Art

The intramedullary rod or nail ("IMR" or "IMN"), also known as Küntscher nail, is a rod placed into the medullary cavity of a bone. These rods have been used to treat fractures of long bones of the body, including the tibia, femur, humerus, and others. IMNs result in earlier return to activity and are "load-sharing" which helps a person place weight on the affected extremity sooner.

The intramedullary nail was initially used by Küntscher in 1939 for use in soldiers in World War II. His design consisted of a long, slender metal cylinder with an open, "cloverleaf" profile. When inserted in medullary canal of a fractured long bone, the nail was then responsible for all load-bearing in the bone as well as stabilizing the fracture site during healing. While innovative, this nail's open profile meant it had very little torsional stability, and a lack of locking screws meant the bone fractures and the nail could move relative to each other and disrupt healing. Since then, the IM nail has undergone radical changes to make it stronger and more stable inside the bone. Contemporary nails now have a closed, cylindrical cross-section and holes for locking screws on the proximal and distal ends of the nail. Patients who receive an IM nail can regain normal use of their limb within 1-2 weeks. The procedure of implanting the nail is minimally invasive and the infection rate is extremely low.

An additional application of the IM nail is to lengthen children's limbs in cases of limb-length discrepency. In these cases, the nails only extend and are not intended to be used with a fractured long bone.

Currently available IM nails are much stronger (in bending stiffness) than the intact bone. Given that bone remodels in response to load, with fundamentally stronger nail inserted, the surrounding bone will decrease its own strength accordingly. Another issue is failure of the locking screws due to repeated concentrated stresses on the screws. Further, because of human size variability there are differences in the length (and width) of the nails which typically requires the stocking of multiple length nails and may require left and right sided devices as well. Since bone length varies with the individual, surgery centers must currently keep an inventory of over 100 different sizes of the same IM nail (see TABLE 1). Furthermore, the sizes are discrete (not continuous), which makes the fit approximate for a substantial proportion of the population. This problem is also manifested in the operating room, when the surgeon must a priori select one nail from inventory for implantation; if the measurement is inaccurate (perhaps due to a highly comminuted fracture), the originally-selected nail must be discarded, creating waste. Post-operative complications of inserting an incorrectly-sized implant include fracture at the time of surgery or insufficient fixation.

TABLE 1

Example Dimensions for Tibial Nails

| Nail | Minimum Length (mm) | Maximum Length (mm) | Minimum Diameter (mm) | Maximum Diameter (mm) | Number of Nail Sizes |
|---|---|---|---|---|---|
| M/DN Tibial Nail (Zimmer) | 180 | 460 | 6 | 15 | 127 |
| Expert Tibial Nail (Synthes) | 255 | 450 | 8 | 13 | 98 |
| Phoenix Tibial Nail (Biomet) | 240 | 420 | 7.5 | 13.5 | 95 |
| T2 Tibial Nail (Stryker) | 240 | 420 | 9 | 15 | 91 |
| ALOD (example dimensions) | 250 | 420 | 10 | 10 | 1 |

Recent advances have modified the conventional nail to change its diameter to fit differently sized medullary canals, yet no reports exist of an IM nail that is adjustable in length. The practical significance of creating a functional intramedullary nail that can adjust its length to match the lengths offered by currently used nails is that surgery centers will reduce their inventory and manufacturers will see decreased production costs. With the ALOD, inventory would be reduced.

Lag and locking screws are frequently used in fracture fixation and other orthopedic surgeries. Like the IMNs, these are manufactured in an array of discrete sizes, which may not be appropriate for any given patient. If the screws used are improperly-sized for the application, there can be intra-operative and post-operative complications. Using a screw that is too long can interfere with tendon gliding if the distal end of the screw exits the cortex; using a screw that is too short can create inadequate purchase into the cortex and thus not have sufficient structural integrity for healing. In either case, additional surgeries may be required to remedy.

Accordingly, there is a continued need for fracture fixation devices that can be easily customized to give a patient-specific fit during orthopedic surgery.

BRIEF SUMMARY OF THE INVENTION

Embodiments of the present invention comprise adjustable length orthopedic devices and systems. According to one embodiment is an adjustable length orthopedic device comprising: (i) an elongated shaft having a longitudinal axis; (ii) an adjustable portion extending from a proximal end of the elongated shaft along the longitudinal axis; and (iii) at least one hole in a distal end portion of the device, the at least one hole adapted for insertion of a pin or screw through the device, wherein a pin inserted through the device is then driven into a bone to anchor the device.

According to an aspect, the interior region of the proximal end of the elongated shaft comprises threads, and wherein an exterior region of the adjustable portion comprises threads, and further wherein the threads of the elongated shaft and the threads of the adjustable portion are complementary such that turning either the elongated shaft or the adjustable portion adjusts the length of the device.

According to another aspect, the adjustable portion comprises an engagement component adapted to allow adjustment of the length of the device by a user.

According to yet another aspect, the length of the device can be adjusted after the device is implanted in a patient.

According to another aspect the device further comprises at least one hole in a proximal end portion of the device. The holes can be oblique relative to the longitudinal axis of the elongated shaft.

According to an aspect, the device further comprises a lag screw, and the length of that lag screw can be adjustable.

According to another embodiment is an adjustable length orthopedic device comprising: (i) an elongated shaft having a longitudinal axis, wherein an interior region of the proximal end of the elongated shaft comprises threads; (ii) an adjustable portion extending from a proximal end of the elongated shaft along the longitudinal axis, wherein an exterior region of the adjustable portion comprises threads, and further wherein the adjustable portion comprises an engagement component adapted to allow adjustment of the length of the device by a user; and (iii) at least one hole in a distal end portion of the device, the at least one hole adapted for insertion of a pin through the device, wherein a pin inserted through the device is then driven into a bone to anchor the device; (iv) wherein the threads of the elongated shaft and the threads of the adjustable portion are complementary such that turning either the elongated shaft or the adjustable portion adjusts the length of the device.

According to another embodiment is an adjustable length orthopedic device comprising: (i) an elongated shaft comprising a central region, the central region comprising an adjustable portion adapted to allow adjustment of the length of the shaft; and (ii) at least one hole in a distal end portion of the device, the at least one hole adapted for insertion of a pin through the device, wherein a pin inserted through the device is then driven into a bone to anchor the device.

According to an aspect, the adjustable portion comprises an engagement component adapted to allow adjustment of the length of the device by a user.

According to another aspect, the length of the device can be adjusted after the device is implanted in a patient.

According to yet another aspect, the device further comprises at least one hole in a proximal end portion of the device. The holes can be oblique relative to the longitudinal axis of the elongated shaft.

According to an aspect, the device further comprises a lag screw, where the length of the lag screw can be adjustable.

According to another embodiment is an adjustable orthopedic device comprising: (i) an elongated shaft having a longitudinal axis; (ii) a lag screw extending from a proximal end of the elongated shaft at an angle oblique to the longitudinal axis, wherein the lag screw comprises a lag screw shaft segment and an adjustable segment, the adjustable segment extending from a proximal end of the shaft segment; and (iii) at least one hole in a distal end portion of the elongated shaft, the at least one hole adapted for insertion of a pin through the device, wherein a pin inserted through the device is then driven into a bone to anchor the device.

According to an aspect, an interior region of the lag screw shaft segment comprises threads, further wherein an exterior region of the adjustable segment comprises threads, and further wherein the threads of the lag screw shaft segment and the threads of the adjustable segment are complementary such that turning the adjustable segment adjusts the length of the lag screw.

According to an aspect, the adjustable segment comprises an engagement component adapted to allow adjustment of the length of the lag screw by a user.

According to another aspect, the length of the lag screw can be adjusted after the device is implanted in a patient.

The details of one or more embodiments are described below and in the accompanying drawings. Other objects and advantages will in part be obvious, and in part appear hereinafter.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Embodiments comprise an adjustable length orthopedic device ("ALOD") with the goal of decreasing inventory and improving patient outcomes by allowing adjustability of the implant to suit each patient. According to an example embodiment, the ALOD comprises an adjustable length intramedullary or cephalomedullary nail, as well as one or more adjustable length locking screws and/or lag screws. The majority of intramedullary nails are between 300 and 400 mm, although many other sizes are possible. Therefore, having one device that may be adjusted in length for this range may be more beneficial than having multiple different sizes in that range to stock.

According to one embodiment, the ALOD is an intramedullary nail utilized to repair a break, fracture, or other injury to a long bone such as the tibia, femur, or humerus, among others. The length of the ALOD can be adjusted before the device is inserted into the patient, after it is inserted into the patient, or both.

According to an embodiment, the ALOD can be locked after it is adjusted and before it is implanted in the patient, in order to prevent unwanted adjustment. There are a variety of mechanisms known for locking, including but not limited to a screw into the implant, a bolt, a keyed slot, or a nut-like object(s) on the distal end of the ALOD.

According to yet an embodiment, the ALOD can be adjusted and/or locked after it is implanted in the patient. For example, the ALOD can be adjusted and/or locked from outside the body with a screw through the nail or a bolt at an adjustable section. The nail may alternatively be locked through distal locking screws while in the body according to techniques and methods known in the art.

According to another embodiment, the ALOD can be locked into the bone with one or more distal locking screws through the implant. These distal locking screws can also optionally have adjustable lengths in order to fit a variety of different bones, patients, and/or operational situations.

Figure 1:
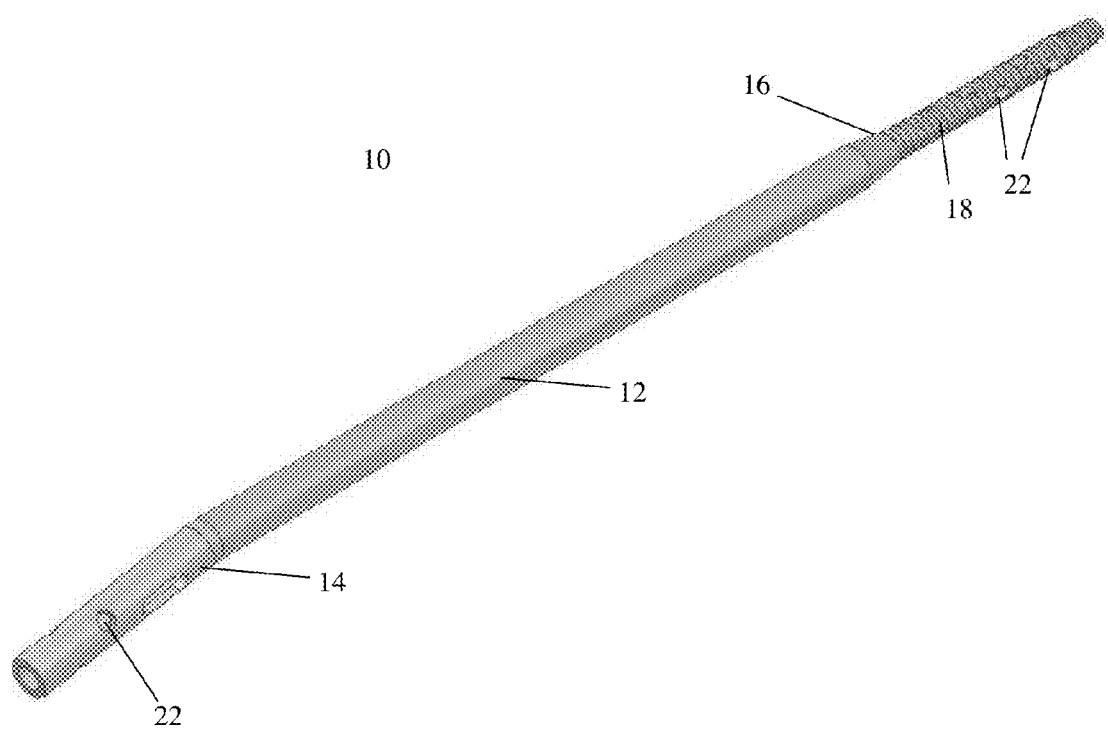
FIG. 1 is a schematic representation of an adjustable length orthopedic device according to an embodiment.
Figure 2:
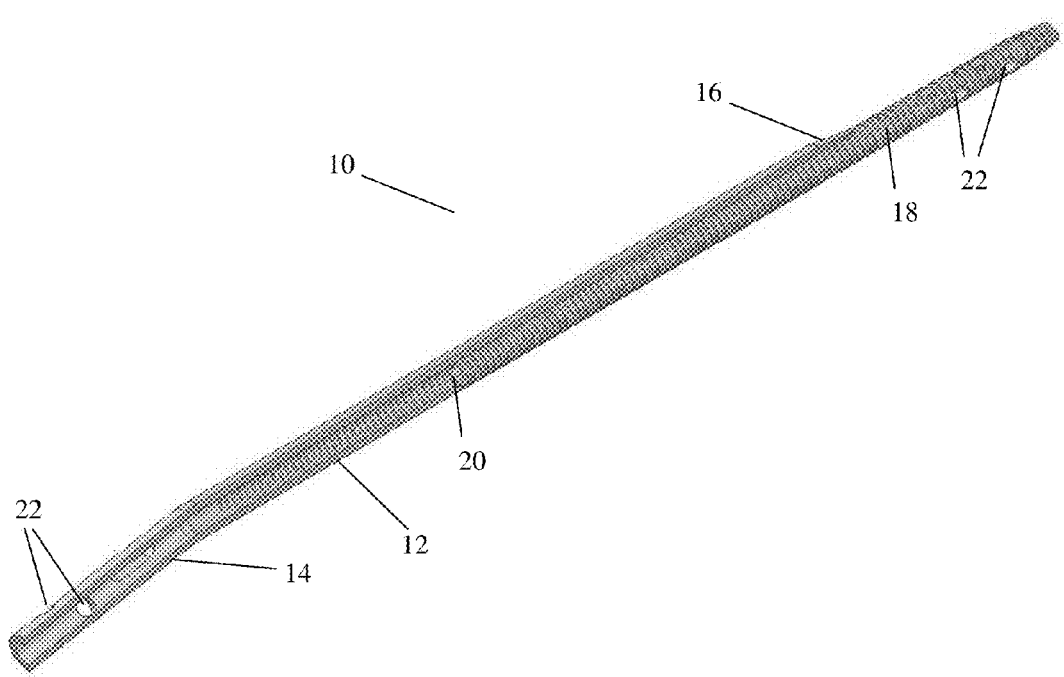
FIG. 2 is a cross-section of the schematic representation of the adjustable length orthopedic device show in FIG. 1, according to an embodiment.

Depicted in FIG. 1 is a schematic representation of an embodiment of an ALOD 10. FIG. 2 is a cross-section of the ALOD embodiment depicted in FIG. 1. In both figures, ALOD 10 comprises a shaft or bow 12 with a proximal end 14 and a distal end 16. Inserted into shaft 12 at distal end 16 is an adjustable section 18. Shaft 12 can be a variety of shapes and sizes, including but not limited to the V-shape or slightly bent shape shown in FIGS. 1 and 2.

Adjustable section 18 is preferably threaded, and preferably has a diameter less than the diameter of shaft 12. All or a portion of the exposed portion of adjustable section 18—the portion outside of shaft 12—can be smooth or can comprise protrusions or other components known in the art to engage bone surfaces.

The threads of adjustable section 18 are complementary to the threads lining all or a portion of the interior of shaft 12 (shown in FIG. 2). In this embodiment, the length of ALOD 10 can be adjusted by rotating one of shaft 12 or adjustable section 18.

According to one embodiment, adjustable section 18 comprises a receptacle, protrusion, or other gripping or receiving component 20 (shown in FIG. 2 at the proximal end, for example) at its proximal and/or distal end that allows a screwdriver or other tool to engage or affix to the adjustable section and either rotate the adjustable section or hole the adjustable section in place as shaft 12 is rotated, thereby elongating or shortening the length of device 10. Rotation (and thus the resulting length modification) can be performed before the ALOD is implanted, after it is implanted, or both.

Figure 4:
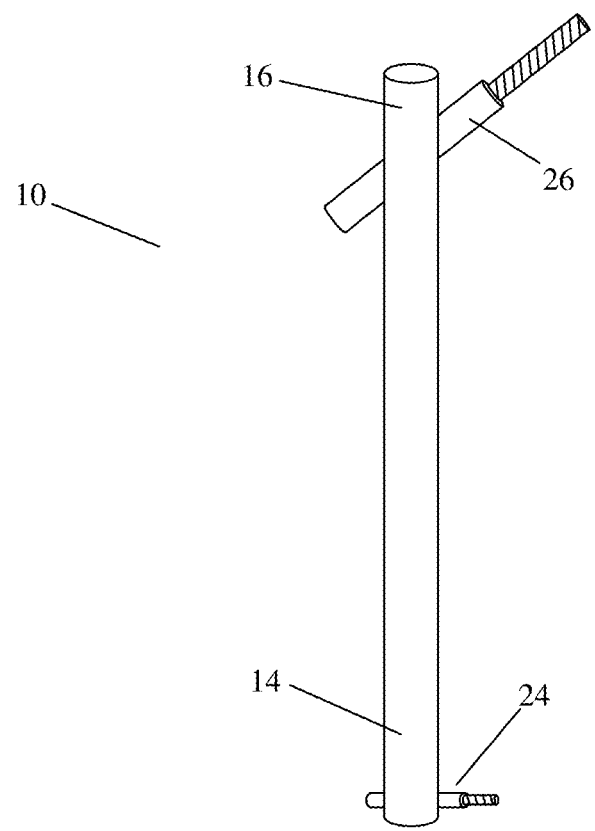
FIG. 4 is a representation of an intramedullary adjustable length orthopedic device according to an embodiment.

The proximal end of shaft 12 and the distal end of adjustable section 18 each preferably comprises one or more holes 22 that allow for locking screws 24 or lag screws 26 to be inserted through the hole and into the bone, as depicted in FIG. 4. Similar to the shaft and adjustable portion of the ALOD, the length of the locking screws and/or lag screws can be made adjustable to allow for the system to fit a variety of patients and bones. Adjustable length screws can be used for screws to be used that are unicortical or bicortical in their application. The ALOD screws can also be used for other orthopedic indications outside of their use with the ALOD rods for the treatment of fractures and other pathologies. Having adjustable screw lengths will increase the accuracy of their length, allow screw use in a locked or bicortical type fashion, and decrease inventory.

According to another embodiment, ALOD 10 comprises a distal component, including but not limited to screws 24, that engage or screw into the bone or deploy in a manner that does not require locking. For example, the component may screw into the intramedullary bone, deploy like an umbrella, or work in a similar way to achieve fixation.

Figure 3:
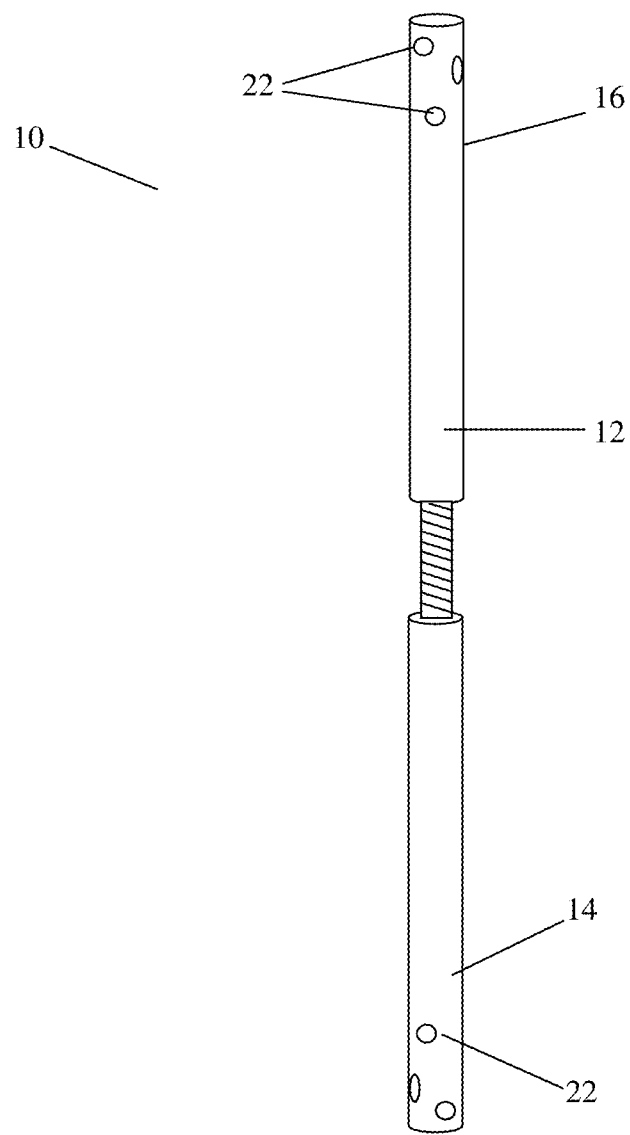
FIG. 3 is a representation of an adjustable length orthopedic device according to an embodiment.
Figure 5:
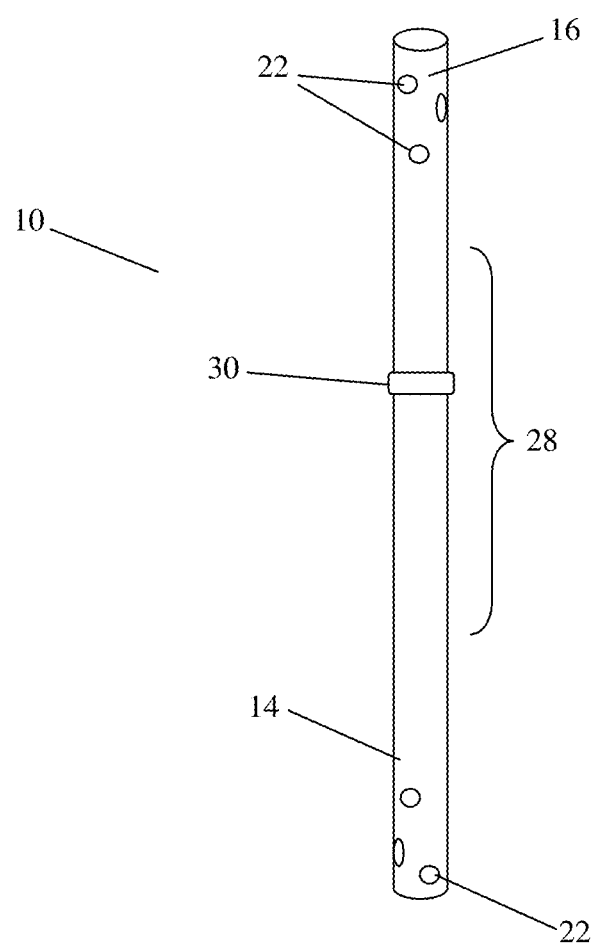
FIG. 5 is a representation of an adjustable length orthopedic device according to an embodiment.

According to another embodiment ALOD 10 is used as a cephalomedullary nail to treat bone fractures, including but not limited to intertrochanteric and subtrochanteric fractures of the femur. According to this embodiment, depicted in FIG. 4, a lag screw 26 is placed through the ALOD 10 (either shaft 12, adjustable section 18, or both) and then inserted into the bone, such as the head of the femur. Typically, one or more screws 24 are used at the distal end of shaft 12 to secure the ALOD in place and preserve proper length and alignment. Although the ALOD structures in FIGS. 3-5 are depicted as straight, it is known in the art that shaft or bow 12 can be straight, curved, or several other shapes. The depictions in the figures do not limit the potential sizes or shapes of the ALOD devices within the scope of the invention or the claims.

According to another embodiment ALOD 10 comprises a central adjustable section, region, or segment 28, an embodiment of which is depicted in FIG. 5. The central adjustable section of the ALOD comprises an adjustment mechanism, including but not limited to an adjustment nut 30, which may be located either inside or outside the patient once the device is implanted. The adjustment mechanism may also comprise, for example, a spring and/or a threaded track that allows the upper and lower segments of the ALOD to move relative to one another.

Figure 6:
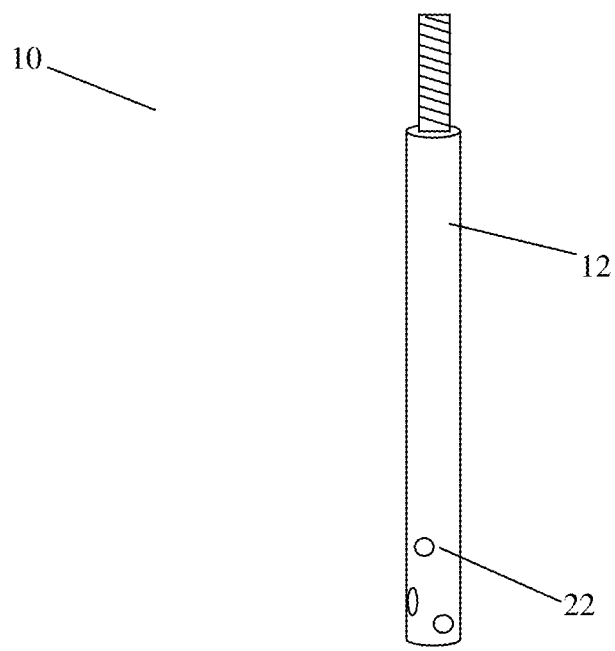
FIG. 6 is a representation of an adjustable length orthopedic device according to an embodiment.

According to yet another embodiment, ALOD 10 does not have to be distally locked, as depicted in FIG. 6. This embodiment comprises a distal segment that screws directly into the bone, or binds into the bone, such that the nail does not require additional screws in the distal region in order to be distally locked.

The ALOD can be used to treat tibia, femur, and humerus fractures, and the design elements can be used to treat other long bone injuries. The ALOD nail has a design that can be scaled for use in all long bones or may be bone specific based on laterality, intramedullary width, and/or anatomy. The technology can thus be used for other long bones such as the radius, ulna, clavicle, fibula, metacarpals, or metatarsals, among others.

Accordingly, the ALOD revolutionizes intramedullary rods and screws in a dramatic way to reduce costs in orthopedic implants. The versatility allows greater length adjustability and specificity, and allows for orthopedic implants to have length adjustments that currently are not available.

Although the present invention has been described in connection with a preferred embodiment, it should be understood that modifications, alterations, and additions can be made to the invention without departing from the scope of the invention as defined by the claims.

What is claimed is:

1. An adjustable length intramedullary orthopedic device configured to reside within the medullary cavity of a bone, the device comprising:
   an elongated shaft having a longitudinal axis extending from a proximal end of the shaft to a distal end of the shaft, the elongated shaft comprising a circular exterior having a first diameter, and wherein the elongated shaft defines a single, circular, threaded elongated interior cavity along a majority of the length of the longitudinal axis, at least a portion of the elongated, circular, threaded interior cavity located at said proximal end, wherein the first diameter is smaller than the diameter of the medullary cavity of the bone;
   an adjustable rod comprising threads, wherein the adjustable rod is threaded into the proximal end of said elongated circular shaft; and
   at least one hole in the distal end portion of the device, said at least one hole adapted for insertion of a pin or screw through the device, wherein the pin is configured to be inserted through said device and into a bone to anchor said device;
   wherein turning either the elongated shaft or the adjustable rod adjusts the length of the device.

2. The adjustable length intramedullary orthopedic device of claim 1, wherein the adjustable portion comprises an engagement component adapted to allow adjustment of the length of the device by a user.

3. The adjustable length intramedullary orthopedic device of claim 1, wherein the device is configured such that the length of the device can be adjusted after said device is implanted in a patient.

4. The adjustable length intramedullary orthopedic device of claim 1, wherein said holes are oblique relative to the longitudinal axis of said elongated shaft.

5. The adjustable length intramedullary orthopedic device of claim 1, further comprising at least one hole in a proximal end portion of the device.

6. The adjustable length intramedullary orthopedic device of claim 1, further comprising a lag screw.

7. The adjustable length intramedullary orthopedic device of claim 1, wherein the length of said lag screw is adjustable.

8. An adjustable length intramedullary orthopedic device configured to reside within the medullary cavity of a bone, the device comprising:
- an elongated shaft extending from a proximal end of the shaft to a distal end of the shaft, the elongated shaft comprising a circular exterior having a first diameter, and wherein the elongated shaft defines a single circular, elongated, threaded interior cavity along a majority of the longitudinal axis at a central region of the shaft, the central region comprising an adjustable portion adapted to allow adjustment of the length of the shaft, wherein the first diameter is smaller than the diameter of the medullary cavity of the bone; and
- at least one hole in the distal end portion of the device, said at least one hole adapted for insertion of a pin or screw through the device, wherein the pin or screw is configured to be inserted through said device and into a bone to anchor said device.

9. The adjustable length intramedullary orthopedic device of claim 8, wherein the adjustable portion comprises an engagement component adapted to allow adjustment of the length of the device by a user.

10. The adjustable length intramedullary orthopedic device of claim 8, wherein the device is configured such that the length of the device can be adjusted after said device is implanted in a patient.

11. The adjustable length intramedullary orthopedic device of claim 8, wherein said holes are oblique relative to the longitudinal axis of said elongated shaft.

12. The adjustable length intramedullary orthopedic device of claim 8, further comprising at least one hole in a proximal end portion of the device.

13. The adjustable length intramedullary orthopedic device of claim 8, further comprising a lag screw.

14. The adjustable length intramedullary orthopedic device of claim 13, wherein the length of said lag screw is adjustable.

* * * * *